(12) United States Patent
Principe

(10) Patent No.: US 7,312,448 B2
(45) Date of Patent: Dec. 25, 2007

(54) METHOD AND APPARATUS FOR QUANTITATIVE THREE-DIMENSIONAL RECONSTRUCTION IN SCANNING ELECTRON MICROSCOPY

(75) Inventor: Edward Principe, Redwood City, CA (US)

(73) Assignee: Carl Zeiss NTS GmbH, Oberkochen (DE)

( * ) Notice: Subject to any disclaimer, the term of this patent is extended or adjusted under 35 U.S.C. 154(b) by 142 days.

(21) Appl. No.: 11/099,489

(22) Filed: Apr. 6, 2005

(65) Prior Publication Data
US 2006/0226359 A1   Oct. 12, 2006

(51) Int. Cl.
*G01N 23/225* (2006.01)
*H01J 37/28* (2006.01)

(52) U.S. Cl. ............ 250/310; 250/307; 250/201.3; 250/461.2; 382/128; 382/131

(58) Field of Classification Search .......... None
See application file for complete search history.

(56) References Cited

U.S. PATENT DOCUMENTS

| | | | |
|---|---|---|---|
| 6,114,695 A * | 9/2000 | Todokoro et al. | 250/310 |
| 6,855,938 B2 | 2/2005 | Preikszas et al. | |
| 7,003,143 B1 * | 2/2006 | Hewitt et al. | 382/128 |
| 7,088,852 B1 * | 8/2006 | Bruce et al. | 382/145 |

FOREIGN PATENT DOCUMENTS

WO   WO2003/071578   8/2003

* cited by examiner

*Primary Examiner*—Jack I. Berman
*Assistant Examiner*—Zia R. Hashmi
(74) *Attorney, Agent, or Firm*—Walter Ottesen

(57) ABSTRACT

A method and an apparatus are for three-dimensional tomographic image generation in a scanning electron microscope system. At least two longitudinal marks are provided on the top surface of the sample which include an angle therebetween. In consecutive image recordings, the positions of these marks are determined and are used to quantify the slice thickness removed between consecutive image recordings.

13 Claims, 3 Drawing Sheets

METHOD AND APPARATUS FOR QUANTITATIVE THREE-DIMENSIONAL RECONSTRUCTION IN SCANNING ELECTRON MICROSCOPY

FIELD OF THE INVENTION

The invention relates to the field of generating tomographic image data sets of a sample in scanning electron microscopy and of generating three dimensional views of the sample.

BACKGROUND OF THE INVENTION

The value of the ability to acquire, interrogate and display n-dimensional data sets has been well established through various scientific disciplines. The biomedical sciences, in particular, have developed sophisticated methods to visualize volumetric image data. However, 3D tomographic data acquisition and volume visualization through the application of serial FIB (Focused Ion Beam) sectioning has only just begun to emerge as a demonstrable method, with work completed by a small number of researchers. The FIB-SEM and FIB-Auger tomographic methods have demonstrated the ability to provide volumetric data resolution down to 10 nm or less, and thus hold tremendous future potential for both material science and biomedical investigations. Yet even the best examples of what have been accomplished thus far in the field of FIB-based nanotomography reflect the fact that this technique is still in the early stages of its development. Regarding prior art in FIB-SEM tomographic methods reference is made to Chapter 14 (Robert Hull) and Chapter 15 (E. L. Principe) and references contained therein, in "Introduction to Focused Ion Beams: Instrumentation, Theory, Techniques and Practice" Giannuzzi, Lucille A.; Stevie, Fred A. (Eds.); Springer-Verlag (2004).

Factors that limit wider utilization of FIB-based tomographic methods include the ease, speed and density of raw data collection. Another obstacle is implementing robust, yet versatile data analysis and volume visualization methods suitable for electron imaging. In principle, the hardware exists for over a decade to collect volumetric image data from a set of sequential FIB serial sections. Yet FIB-based nanotomography has, until now, remained a less practical application due to the time, effort and specialized data reduction expertise involved.

The methods of quantifying cross sectional slices obtained by FIB disclosed until now require either a measurement of each frame image perpendicularly to its cross section to measure the thickness of the material removed or another method to quantify based upon the cross sectional images. The first method requires, however, either achieving a perpendicular view through another image recording system and/or moving the sample to achieve the perpendicular view.

More recently, for example, in U.S. Pat. No. 6,855,938, systems have been disclosed which can be used for FIB-SEM tomographic methods.

SUMMARY OF THE INVENTION

In view of the above, it is an object of the invention to provide a method for generating three dimensional image data of a sample in a scanning electron microscope. A second object of the invention is to provide a charged particle beam system which is capable of generating three dimensional image data of a sample.

According to a first concept of the invention, the first object is solved by a method for generating three dimensional tomographic image data of a sample with a scanning electron microscope comprising the steps of:

a) providing on a surface of the sample, two longitudinal marks having a distance between the marks whereby the distance is varying in a selected direction of the surface;

b) removing a slice from the sample by a beam of charged particles scanning across the sample in a direction perpendicular to the selected direction;

c) scanning the sample by a primary electron beam, the primary electron beam having a direction of propagation not perpendicular to the selected direction, and recording image data by detecting electrons emitted by the sample and storing the image data as a set of image data;

d) repeating step b) and step c) for a plurality of times and generating a plurality of sets of image data; and, e) analyzing the stored image data to identify the marks in each set of image data and calculate a thickness of the slice from the distance of the marks in the respective set of image data.

According to a second concept of the invention, the second object is realized by a charged particle beam system comprising: an electron source; an electron optical system including at least one electron optical lens defining an electron optical axis and at least one deflection system, wherein the at least one electron optical lens generates an electron probe by electrons emitted by the electron source and the deflecting system provides a deflection of the electron probe in a direction perpendicular to the electron optical axis; an electron detector; a multiple image memory capable of storing a plurality of data sets of image data generated by the electron detector; an image analysis system; wherein the image analysis system is designed to analyse image data stored in the image memory to identify positions of marks in each set of image data stored in the multiple image memory, to calculate distance values between each set of image data and a next neighbored set of image data on the basis of the identified positions of the marks, and to assign the distance values to the stored plurality of data sets of image data; and a display system capable of generating various desirable three dimensional views of the plurality of data sets of image data using the distance values.

According to the method of the present invention two longitudinal, non-parallel marks are provided to the sample surface. Afterwards a series of images of the sample are recorded with a step of removing a slice from the sample between each two recordings. The varying positions of the marks in the series of images which are recorded are evaluated and used as a measurement for the thicknesses of the slices removed. The thickness of each slice then is assigned to the respective recorded image to define information about the position of the slice within the sample in the direction perpendicular to the slice. With these data available, arbitrary 3D displays of the sample can be generated and displayed.

BRIEF DESCRIPTION OF THE DRAWINGS

In the following, embodiments of the invention are explained in further detail with reference to the drawings, wherein.

DESCRIPTION OF THE PREFERRED
EMBODIMENTS OF THE INVENTION

Figure 1:
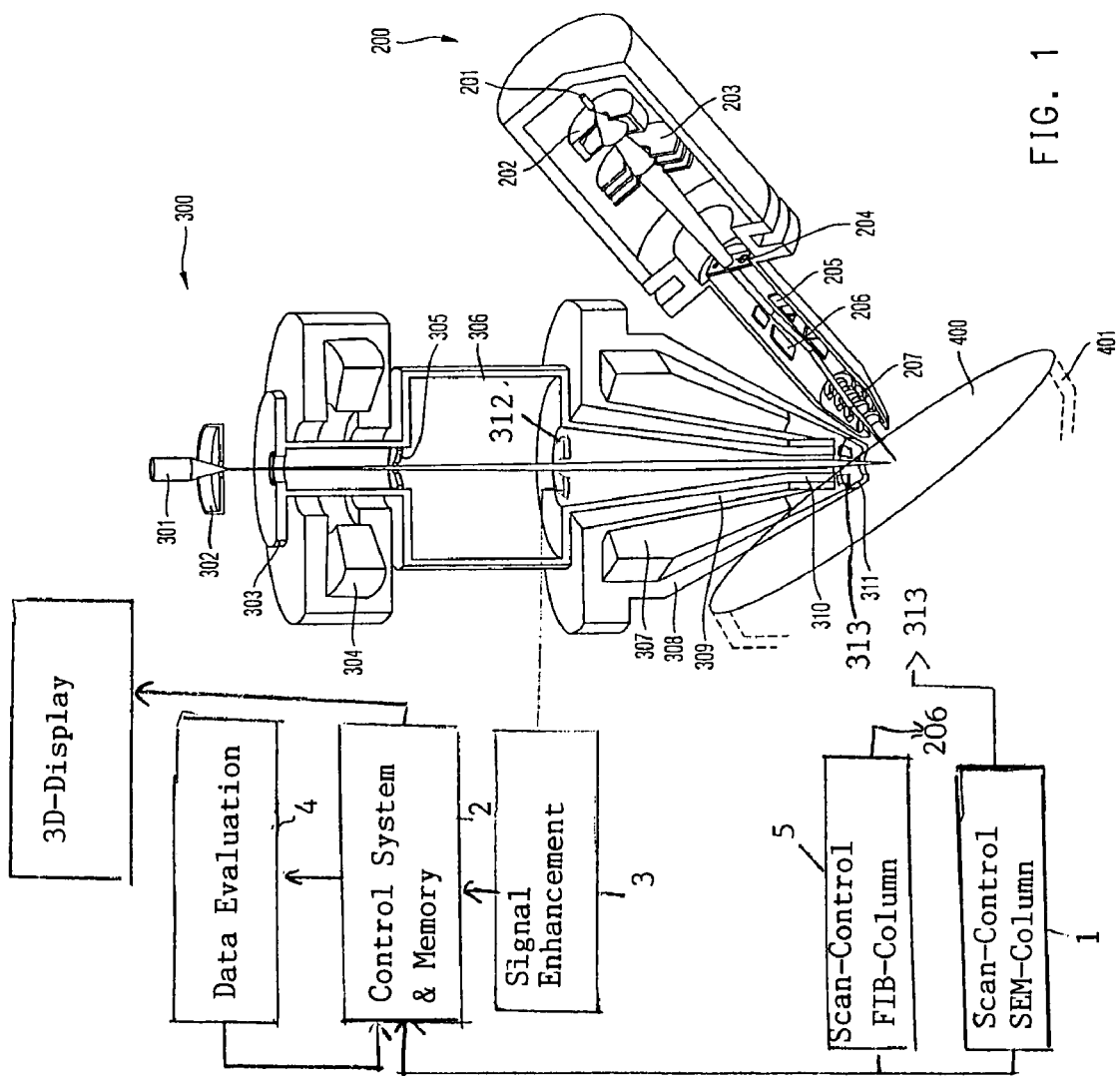
FIG. 1 is a schematic representation of a system according to the invention.

The charged particle beam system in FIG. 1 comprises a scanning electron beam column 300 and a focused ion beam column 200. As shown in FIG. 1, the optical axis of the electron beam column 300 and of the focused ion beam column 200 intersects substantially in a plane defined by the planar surface of a sample 400. The optical axis of the focused ion beam column extends approximately perpendicularly to this plane of the sample 400 and the ion beam therefore impinges orthogonally on this surface. The angle at which the electron beam impinges on this surface of the sample 400 in this configuration is about 35°.

In the scanning electron beam column 300, a primary electron beam is generated by an electron source 301, preferably a Schottky field emitter, and an anode 303. The emitted electrons also pass through an extractor electrode 302 disposed between said electron source 301 and the anode 303. The accelerated electron beam then passes through a bore at the bottom of the anode 303 and is substantially collimated by a collimator system 304 designed by a magnetic lens. After having passed through an aperture stop 305, the electron beam passes through an inner space 306 of the electron beam column in which a detector 312 for secondary or backscattered electrons is arranged.

Following in the beam direction of the electrons, an objective lens is provided which is a combination of a magnetic lens and an electrostatic lens. The electron beam is focused by this lens on the surface of the sample 400. The magnetic portion of the objective lens is formed by an outer pole piece 308 and an inner pole piece 309 as well as a coil body 307 disposed therebetween. The electrostatic portion of the objective lens is defined by two electrodes 310 and 311 which are arranged or end in the region of the pole piece gap of the magnetic lens portion. In the region of the pole piece gap of the magnetic lens portion, additional saddle coils 313 are disposed symmetrically about the beam path for deflecting the electron beam perpendicularly to the optical axis of the electron beam column which is defined by the axis to which the electron beam column is rotationally symmetric. By deflecting the electron beam, the sample 400 can be scanned by the electron probe defined by the focus of the electron beam.

The ion beam column 200 comprises an ion source 201 which comprises a configuration with a drop of liquid gallium at the tip thereof from which an ion beam is extracted by means of an extraction electrode 202. When passing through the ion optics of the FIB column 200, the ion beam successively passes through a condensor 203, a variable stop 204, a set of electrodes 205 and 206 for deflecting and orienting the ion beam and finally an arrangement of beam shaping individual lenses 207, before the ion beam exits from the FIB column.

The pole pieces of the magnetic portion of the objective lens of the scanning electron beam column 300 are designed in a manner that no or nearly no magnetic fields are generated outside the objective lens so that the ion beam emitted by the FIB column is not disturbed by any magnetic stray field of the objective lens of the electron beam column.

The system described to this point is disclosed in U.S. Pat. No. 6,855,938 which is incorporated herein by reference with respect to further details of the design of the electron optical system and the ion optical system.

At the left side of FIG. 1, some of the control elements of the system are shown. A scan control 1 generates a scanning signal which is applied to the saddle coils 313 of the electron beam column and a second scan control 5 generates a scanning signal which is applied to the deflection electrode 206 of the FIB column. The signal of the scan control 1 also is applied to a data memory 2 and triggers this data memory 2. The data memory 2 has a capacity of several gigabytes to store a plurality of image data sets.

Secondary and/or back scattered electrons emitted by the sample 400 because of the primary electron beam are accelerated by the electrostatic lens portion of the objective lens of the scanning electron beam column in the direction of the optical axis of the electron beam column and are detected by the detector 312. The signals detected by detector 312 are enhanced by a signal enhancement unit 3 and stored in data memory 2 in combination with assigned information from the scan control 1.

By deflecting the focused ion beam, preferably in a direction perpendicular to the plane which is defined by the optical axis of the electron beam column and the optical axis of the ion beam column (drawing plane in FIG. 1), using the scan control 5, thin slices are removed from the sample 400. Simultaneously, image data are generated by using the scanned electron beam and detecting secondary and/or back scattered electrons. The image data generated by the electron beam column within the time in which one slice is removed defines one image data set. By repeatedly removing one slice after the other and continuously generating image data a plurality of sets of image data are recorded and stored in the memory 2.

Figure 2:
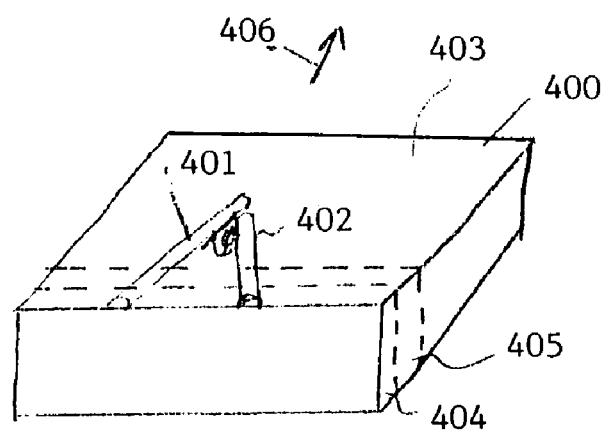
FIG. 2 is a perspective view on a sample provided with two longitudinal marks.
Figure 3:
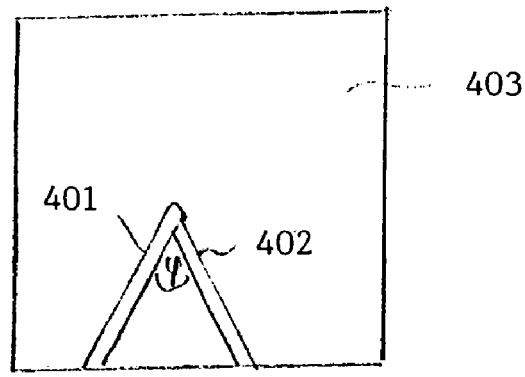
FIG. 3 is a plan view on the sample of FIG. 2.

In a further step, the plurality of sets of image data stored in memory 2 are evaluated in a data evaluation unit 4. Regarding the evaluation, reference is made to FIGS. 2 to 4.

According to the invention, two longitudinal marks 401 and 402 are provided on the surface 403 of the sample before the 3D tomographic data are recorded. The marks 401 and 402 are at a distance from each other which is varying in a direction perpendicular to the plane of the slices which are to be removed by the focused ion beam from the sample 400. Accordingly, the two fiducial marks define an angle φ therebetween. The marks can be either made by deposition on the surface of the sample or by etching. However, to receive as much resolution as possible, it is most preferable to make the marks 401 and 402 directly by the system of the invention either by deposition of ions from the FIB column or by etching two longitudinal marks 401 and 402 by a sputtering process by means of the focused ion beam by scanning the focused ion beam in the desired direction, almost perpendicular to the scanning direction of the ion beam during the removal of the slices, by the deflection electrode 206. An alternative is to make the marks 401 and 402 by electron beam induced etching or electron beam induced deposition of gas atoms which are brought into the region of the sample by gas nozzles as disclosed, for example, in international patent application PCT/EP 03/01923, filed Feb. 25, 2003 (WO 03/071578), and filed in the under U.S. Ser. No. 10/923,814, the entire content of which is incorporated herein by reference. In the latter case, the marks 401 and 402 are written by deflecting the electron beam of the electron beam column 300 via the saddle coils 313.

Because the marks 401 and 402 include an angle therebetween, the position of the marks in each image data set varies after each slice 404, 405 is removed. By identifying the positions of the marks 401 and 402 at the actual front edge of the slices 404, 405 and comparing their positions in consecutive image data sets, these position values define an exact measure of the thickness of each slice 404, 405 in the direction 406 perpendicular to the slice planes, that is, perpendicular to the two longer sides of the slices.

Figure 4:
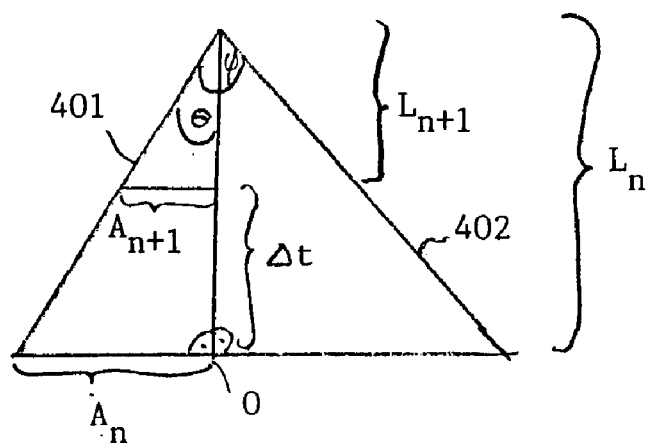
FIG. 4 shows the relationship of similar triangles used for determining the thickness of the slice from the positions of the longitudinal marks; and, FIG. 5 is a block diagram showing the various steps in a method according to the invention.

The evaluation of the slice thickness can be performed by comparing similar triangles as shown in FIG. 4. If again with 401 and 402 the two marks are depicted and Δt defines the slice thickness, this slice thickness can be determined according to the equation:

$$\Delta t = (A_n - A_{n+1})/\tan \theta$$

from the positions $A_{n+1}$ and $A_n$ of the mark 401 in the respective consecutive images n and n+1 from an arbitrarily defined zero point 0 and the angle θ which this longitudinal mark 401 includes with an axis perpendicular to the slice plane. Both positions $A_{n+1}$ and $A_n$ and the angle θ can be easily determined in the SEM image data sets. In principle therefore only one mark 401 would be necessary to determine the slice thickness Δt, however to exactly identify the position of each image data set to the other image data set also the second mark 402 has to be identified in each image data set so that from both positions the crossing of both marks 401 and 402 can be determined. This crossing then defines an identical and unique zero point for all image data sets.

Figure 5:
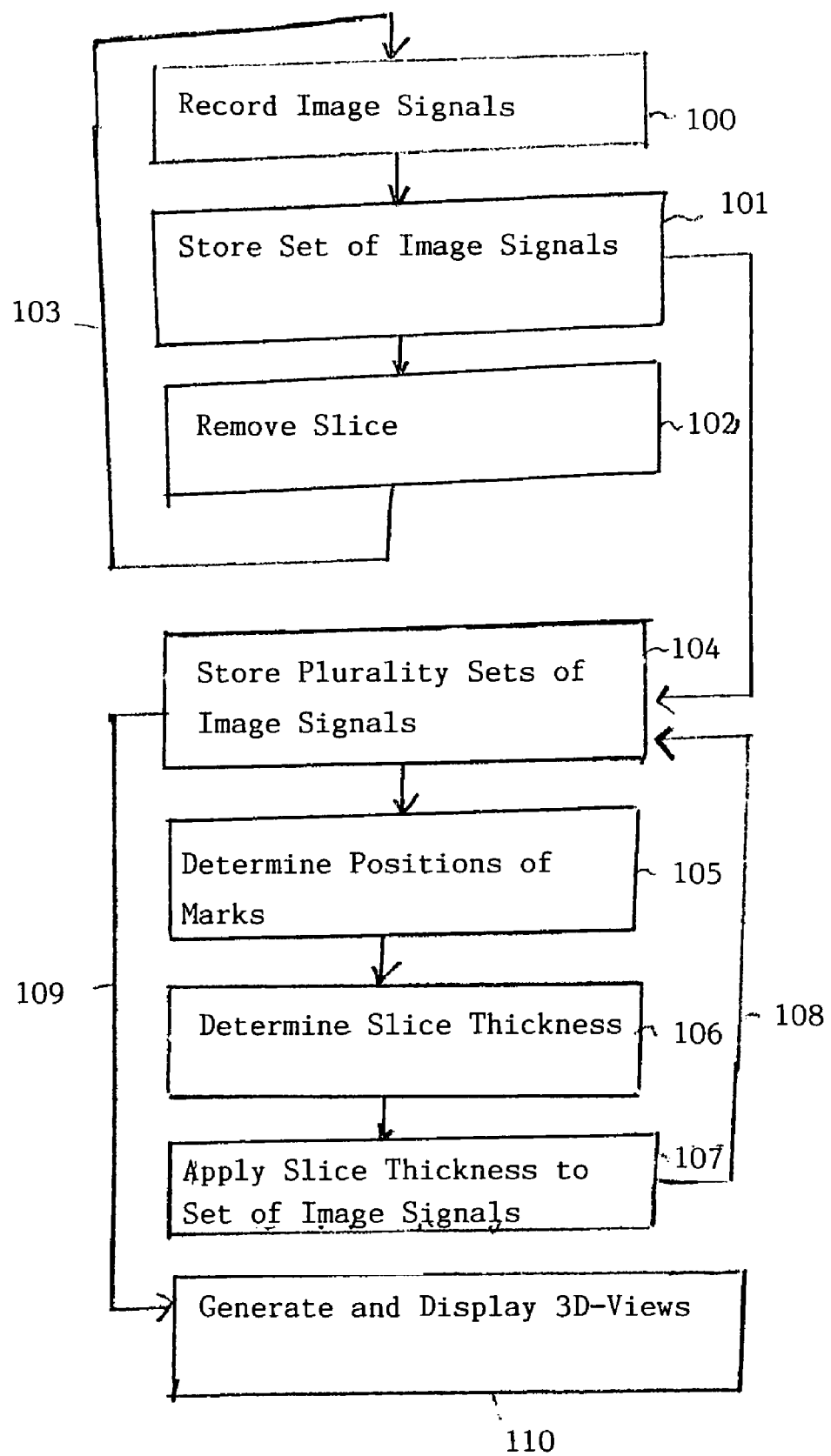

In the block diagram of FIG. 5, the main process steps in the system of the invention are shown. In step 100, image data signals of an SEM image are recorded during scanning the electron beam of the electron optical column in two directions perpendicular to its optical axis and detecting secondary or back scattered electrons. In a consecutive step 101, this set of image data is stored in an image memory. During the time the image data set is recorded in step 102, a slice is removed from the sample by dry etching or sputtering of the sample by the focused ion beam. These steps 100 through 102 are repeated for a desired number of times which is denoted by recursive arrow 103 until a desired plurality of sets of image data are stored in the memory as denoted by step 104.

After the desired number of sets of image data are recorded in step 104 in a following step 105, the positions of the marks in each set of image data are determined. From the positions of the marks in consecutive sets of image data in step 106, the slice thicknesses are determined as well as the lateral positions of the sets of image data (that is, in the plane of the slices) are determined. These position data are assigned in a step 107 to each set of image data and also stored in the memory as denoted by arrow 108.

After the above steps have been performed, sufficient information to generate high resolution 3D image displays according to usual and known display methods are available. Therefore in a step denoted by arrow 109, arbitrary portions of the information stored in the memory can be read out to generate in step 110 the desired arbitrary 3D view of the sample and to display it.

As disclosed above, the present invention shows that with the advent of high-resolution simultaneous SE imaging during the FIB sectioning process, it is now practical to acquire several hundred SEM image frames in the span of less than one hour in an automated fashion. It can be demonstrated that live imaging (that is, generating of image data during FIB processing of the sample) coupled with automated image recording facilitates the data acquisition process significantly, while easily providing lateral resolution at the nanometer scale. In addition, the high collection density translates to similar resolution along the direction normal to the cutting plane (that is, perpendicular to the plane of the slices) over a depth of several microns and greater.

The live data acquisition method is coupled to a data reduction process that allows convenient display of the high quality volume reconstructions through animated section sequences, exploration of sub-volumes and application of selective transparency.

As shown above, with the method and apparatus of the invention, SEM image data are quantified in three dimensions. The method described above employs a simple yet effective method to quantify the slice thickness of each set of image data (that is, image frame) using a geometrical relationship between the image slice thickness and the cross sectional image; images recorded under different views are not necessary.

With the method and system of the invention, recording of 3D image data sets is at least a factor of five quicker in comparison to state of the art systems and methods. It can be shown that with the method and system of the invention, 400 image frames can be recorded within one hour. This translates to a significantly higher depth resolution, on the order of 5-20 nm, depending on acquisition conditions only determined by the operator of the system.

The system and method of the invention do not necessitate any image movement during the complete data acquisition which would interrupt the data acquisition. Because the sample is not moved during the complete data acquisition translational and rotational errors are minimized and data acquisition is accelerated to its maximum. The continuous nature of the process also means that the image data of the slices are more uniform in nature and less subject to thickness variations and realignment errors associated with stopping and restarting the tomographic data acquisition process.

The "chevron fiducial" mark process of the invention allows quantification based upon either an average image slice thickness over the entire data acquisition or based upon thicknesses in each individual image data set. The ability to image and identify the mark on the cross section in a single view improves speed of data acquisition and accuracy of the data. The data can be processed after all image data have been acquired and does not require any prior knowledge of the sample, the sample sputter rate or any other properties of the sample, nor any other calibration or measurement during the data acquisition process.

The marks in principle can be etched into or deposited onto the sample surface either with the sample installed to the system of the invention or by any other method. The marks can be either recesses (that is, etched into) or raised (that is, deposited) with respect to the sample. If the marks are deposited they can consist of any suitable material, oxide, metal, organic, inorganic or any combination thereof. The only requirement is that the marks have a defined and known geometric relationship between a top view on the sample surface on which the marks are provided and the cross sectional image of the sample, that is, perpendicular to the sample surface. The most direct approach is a pattern consisting of two straight lines forming a known angle etched into the sample surface perpendicularly to the cross section of the sample. As the angle of the lines is known a simple mathematical relationship can be established based upon the law of similar triangles.

As an alternative, also nested marks can be used with different angles if desired to enhance the accuracy over a shorter dimension. For instance, a third angled line could be added; the greater angle between the lines then leads to a greater rate of change in the position of the marks viewed in consecutive cross sectional images.

In the terms of the geometry above, the lines could be at any length and angle selected by the operator of the system.

It is understood that the foregoing description is that of the preferred embodiments of the invention and that various changes and modifications may be made thereto without departing from the spirit and scope of the invention as defined in the appended claims.

What is claimed is:

1. A method for generating three dimensional tomographic image data of a sample with a scanning electron microscope, the method comprising the steps of:
   a) providing on a surface of the sample, two longitudinally extending marks having a distance between respective sections of said longitudinally extending marks whereby said distance is varying in a selected direction of said surface;
   b) removing a slice from said sample by a beam of charged particles scanning across said sample in a direction perpendicular to said selected direction;
   c) scanning said sample by a primary electron beam, said primary electron beam having a direction of propagation not perpendicular to said selected direction, and recording image data by detecting electrons emitted by said sample and storing said image data as a set of image data;
   d) repeating said step b) and said step c) for a plurality of times and generating a plurality of sets of image data; and,
   e) analyzing said stored image data to identify said respective sections of said longitudinally extending marks in each set of image data and calculate a thickness of said slice from said distance of said respective sections of said longitudinally extending marks in said respective set of image data.

2. The method of claim 1, wherein said slice has long extensions in directions perpendicular to said selected direction and a short extension in said selected direction.

3. The method of claim 1, wherein, in an additional step, a length of one of the longitudinally extending marks and an angle between one of the longitudinally extending marks and the selected direction are determined.

4. The method of claim 3, wherein said calculation of the thickness of the slice is performed on the basis of comparing similar triangles.

5. The method of claim 1, wherein said charged particle beam is a focused ion beam.

6. The method of claim 1, wherein said charged particle beam is a focused electron beam and wherein an electron beam activatable gas is provided to a region whereat said focused electron beam impinges on said sample.

7. The method of claim 5, wherein said removing step and said scanning step are performed simultaneously.

8. The method of claim 5, wherein said two longitudinally extending marks are generated by ion beam induced deposition of ions in said focused ion beam.

9. The method of claim 5, wherein said two longitudinally extending marks are generated by ion beam etching.

10. A charged particle beam system comprising:
    an electron source;
    an electron optical system including at least one electron optical lens defining an electron optical axis and at least one deflection system, wherein said at least one electron optical lens generates an electron probe by electrons emitted by said electron source and said deflecting system provides a deflection of said electron probe in a direction perpendicular to said electron optical axis;
    an electron detector;
    a multiple image memory for storing a plurality of data sets of image data generated by said electron detector;
    an image analysis system;
    said image analysis system functioning: to analyze image data stored in said image memory to identify positions of respective sections of longitudinally extending marks in each set of image data stored in said multiple image memory, to calculate distance values between each set of image data and a next neighboured set of image data on the basis of said identified positions of said respective sections of said longitudinally extending marks; and, to assign said distance values to said stored plurality of data sets of image data; and,
    a display system for generating various desirable three dimensional views of said plurality of data sets of image data using said distance values.

11. The charged particle system of claim 10, further comprising an ion source and an ion optical system; said ion optical system defining an ion optical axis along which an ion beam of ions emitted by said ion source runs; and, said ion optical axis being inclined with respect to said electron optical axis.

12. The charged particle system of claim 11, wherein said at least one electron optical lens is designed to be magnetically field-free in regions in which said ion beam runs.

13. The charged particle system of claim 12, wherein said electron optical lens comprises an electrostatic objective lens.

* * * * *

UNITED STATES PATENT AND TRADEMARK OFFICE
CERTIFICATE OF CORRECTION

PATENT NO. : 7,312,448 B2 Page 1 of 1
APPLICATION NO. : 11/099489
DATED : December 25, 2007
INVENTOR(S) : Edward Principe It is certified that error appears in the above-identified patent and that said Letters Patent is hereby corrected as shown below:

Column 4:
Line 63: delete "the under U.S." and substitute -- the U.S. under -- therefor.

Column 5:
Line 12: delete "At" and substitute -- $\Delta t$ -- therefor.

Signed and Sealed this

Twenty-ninth Day of April, 2008

JON W. DUDAS
*Director of the United States Patent and Trademark Office*